(12) United States Patent
Anderson et al.

(10) Patent No.: US 10,076,348 B2
(45) Date of Patent: *Sep. 18, 2018

(54) ROTARY INPUT FOR LEVER ACTUATION

(71) Applicant: Intuitive Surgical Operations, Inc., Sunnvale, CA (US)

(72) Inventors: S. Christopher Anderson, San Francisco, CA (US); Thomas G. Cooper, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1062 days.

This patent is subject to a terminal disclaimer.

(21) Appl. No.: 14/461,260

(22) Filed: Aug. 15, 2014

(65) Prior Publication Data

US 2015/0051618 A1 Feb. 19, 2015

Related U.S. Application Data

(60) Provisional application No. 61/866,239, filed on Aug. 15, 2013.

(51) Int. Cl.
*A61B 17/28* (2006.01)
*A61B 34/00* (2016.01)
*A61B 34/30* (2016.01)
*A61B 17/00* (2006.01)

(52) U.S. Cl.
CPC .............. *A61B 17/28* (2013.01); *A61B 34/30* (2016.02); *A61B 34/71* (2016.02); *A61B 2017/00477* (2013.01)

(58) Field of Classification Search
CPC .................... A61B 17/28; A61B 34/30; A61B 2017/00477; A61B 34/71; A61B 17/00234; A61B 34/70
USPC .......................................... 600/184; 606/130
See application file for complete search history.

(56) References Cited

U.S. PATENT DOCUMENTS 9,839,439 B2 * 12/2017 Cooper .................. A61B 17/28

OTHER PUBLICATIONS

Vertut, Jean, et al., "Robot Technology; vol. 3A Teleoperation and Robotics Evolution and Development"; 1986 Prentice-Hall, Inc.; Englewood Cliffs, NJ.

* cited by examiner

*Primary Examiner* — Christopher D Koharski
*Assistant Examiner* — Roland Dinga

(57) ABSTRACT

A surgical instrument includes a surgical end effector coupled to an elongate tube and a rod that passes through the elongate tube. A control mechanism coupled to the elongate tube includes an input axle having a first axis of rotation, an idler pulley having a second axis of rotation perpendicular to the first axis, and a lever coupled to the rod and having a third axis of rotation parallel to the second axis. First and second capstans are fixed to the input axle. Cables pass over the idler pulley and are coupled to the lever. Rotating the input axle in a first direction winds a first cable onto the first capstan, rotates the lever, and moves the rod in a second direction. Rotating the input axle opposite the first direction winds a second cable onto the second capstan, rotates the lever, and moves the rod opposite the second direction.

22 Claims, 4 Drawing Sheets

ROTARY INPUT FOR LEVER ACTUATION

BACKGROUND

Field

Embodiments of the invention relate to the field of force transmissions; and more specifically, to force transmissions for use in surgical instruments intended for use in teleoperated minimally invasive surgeries.

Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor. In teleoperated minimally invasive surgery, the surgeon manipulates the tissues by using mechanically actuated end effectors of the elongated surgical instruments. Mechanical actuation may allow for improved control of the surgical instruments.

The mechanically actuated surgical instruments will generally have an end effector in the form of a surgical tool such as a forceps, a scissors, a clamp, a needle grasper, or the like at a distal end of an elongate tube. A flexible rod may extend from the end effector to a proximal control mechanism that pushes and pulls the rod to provide an actuating force to open and close the end effector.

Rotary actuators, such as servo motors, are an effective way to provide controlled actuation forces to the proximal control mechanism. The proximal control mechanism then translates the rotary input force into the push-pull motion needed to control the opening and closing of the end effector. The proximal control mechanism may receive many such rotary inputs, perhaps six to eight, each of which can be translated into an appropriate motion for controlling some aspect of the end effector. It is desirable that the proximal control mechanism be compact to avoiding crowding in the surgical field.

In view of the above, it is desirable to provide an improved apparatus and method for transmitting rotary actuating forces to a push-pull rod in an elongate tube of a surgical instrument intended for use in teleoperated minimally invasive surgeries.

SUMMARY

A mechanically actuated surgical instrument includes a surgical end effector coupled to an elongated tube. A rod is coupled to the surgical end effector and passes through the elongated tube. A proximal control mechanism coupled to the elongated tube includes an input axle having a first axis of rotation, an idler pulley having a second axis of rotation perpendicular to the first axis, and a lever coupled to the rod and having a third axis of rotation substantially parallel to the second axis. First and second capstans are fixed to the input axle. A first cable passes over the idler pulley and is coupled to the lever such that rotating the input axle in a first direction winds the first cable onto the first capstan, rotates the lever, and moves the rod in a second direction. A second cable passes over the idler pulley and is coupled to the lever such that rotating the input axle in a third direction opposite the first direction winds the second cable onto the second capstan, rotates the lever, and moves the rod in a fourth direction opposite the second direction.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figures 1, 2:
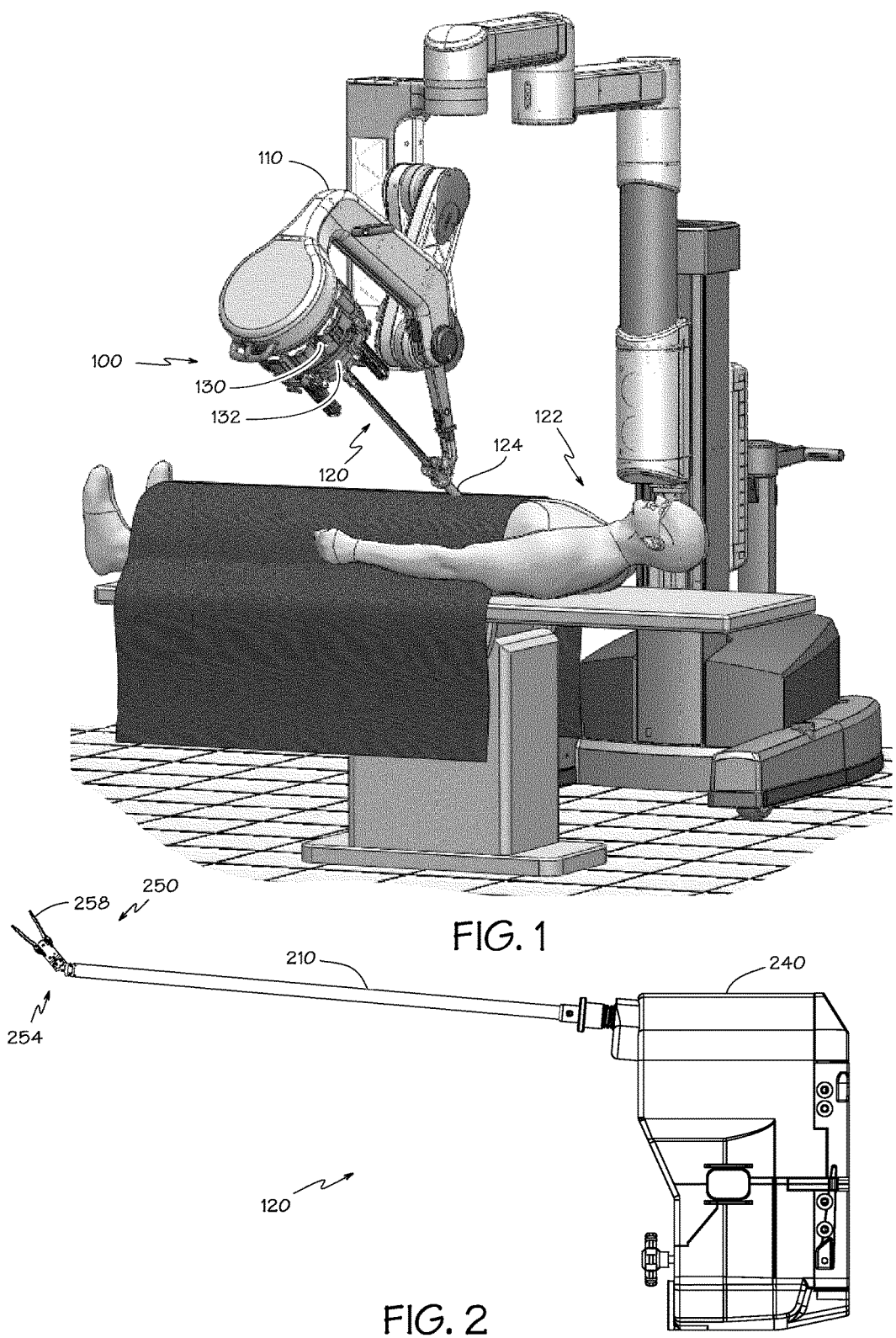
FIG. 1 is a simplified perspective view of a teleoperated surgical system with a mechanically actuated surgical instrument inserted through a port in a patient's abdomen.
FIG. 2 is a plan view of a surgical instrument for use with a mechanically actuated manipulator.

FIG. 1 is a simplified diagrammatic perspective view of a teleoperated surgical system 100. The teleoperated surgical system 100 includes a support assembly 110 mounted to or near an operating table supporting a patient's body 122. The support assembly 110 supports one or more surgical instruments 120 that operate on a surgical site within the patient's body 122.

The term "instrument" is used herein to describe a device configured to be inserted into a patient's body and used to carry out surgical procedures. The instrument includes a surgical tool, such as a forceps, a needle driver, a shears, a monopolar cauterizer, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support for the surgical tool so that the position and orientation of the surgical tool can be manipulated.

The simplified perspective view of the teleoperated surgical system 100 shows only a single surgical instrument 120 to allow aspects of the invention to be more clearly seen. A functional teleoperated surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, marketed by Intuitive Surgical, Inc., of Sunnyvale Calif.

A functional teleoperated surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control motors, such as servo motors, which, in turn, control the articulation of the surgical assembly. The forces generated by the motors are transferred via drivetrain mechanisms, which transmit the forces from the motors generated outside the patient's body 122 through an intermediate portion of the elongate surgical instrument 120 to a portion of the surgical instrument inside the patient's body 122 distal from the motor. Persons familiar with telemanipulative, teleoperative, and telepresence surgery will know of systems such as the da Vinci® Surgical System and the Zeus® system originally manufactured by Computer Motion, Inc. and various illustrative components of such systems.

The surgical instrument 120 is shown inserted through an entry guide 124, e.g., a cannula in the patient's abdomen. A functional teleoperated surgical system may provide an entry guide manipulator (not shown; in one illustrative aspect the entry guide manipulator is part of the support assembly 110) and an instrument manipulator (discussed below). The entry guide 124 is mounted onto the entry guide manipulator, which includes a mechanically actuated positioning system for positioning the distal end of the entry guide 124 at the desired target surgical site. The mechanically actuated positioning system may be provided in a variety of forms, such as a serial link arm having multiple degrees of freedom (e.g., six degrees of freedom) or a jointed arm that provides a remote center of motion (due to either hardware or software constraints) and which is positioned by one or more unpowered, lockable setup joints mounted onto a base. Alternatively, the entry guide manipulator may be manually maneuvered so as to position the entry guide 124 in the desired location. In some telesurgical embodiments, the input devices that control the manipulator (s) may be provided at a location remote from the patient (outside the room in which the patient is placed). The input signals from the input devices are then transmitted to the control system, which, in turn, manipulates the instrument manipulators 130 in response to those signals. The instrument manipulator may be coupled to the entry guide manipulator such that the instrument manipulator 130 moves in conjunction with the entry guide 124.

The surgical instrument 120 is detachably connected to the mechanically actuated instrument manipulator 130. The mechanically actuated manipulator includes a coupler 132 to transfer controller motion from the mechanically actuated manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

FIG. 2 is a plan view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical devices such as the forceps 258 shown, a needle driver, a cautery device, a cutting tool, an imaging device (e.g., an endoscope or ultrasound probe), or a combined device that includes a combination of two or more various tools and imaging devices. Surgical devices that provide an opening and closing motion, such as the forceps 258 shown, may be coupled to a rod that passes through the elongate tube 210 and into the proximal control mechanism 240. The proximal control mechanism translates input from an actuator to push and pull on the rod to open and close the surgical device.

Figure 3:
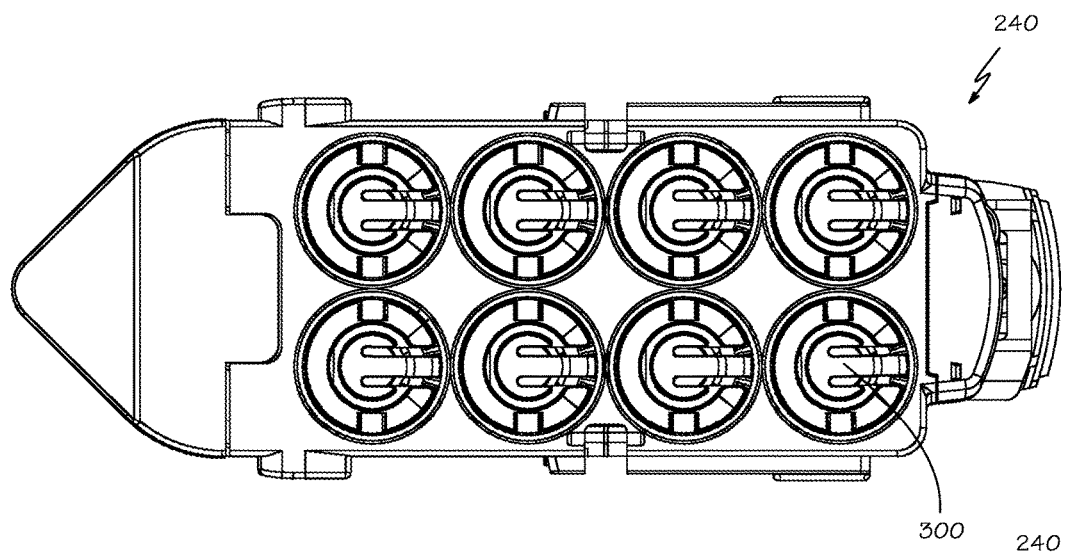
FIG. 3 is a top view of the surgical instrument of FIG. 2 showing the input connections that connect to actuators.

FIG. 3 is a top view of the proximal control mechanism 240 for the surgical instrument of FIG. 2 showing the input connections 300 that connect to actuators (not shown). The actuators used with embodiments of the invention are rotary actuators, such as servo motors. The proximal control mechanism of the surgical instrument may provide input connections for a number of actuators with each actuator controlling one motion of the surgical tool. For example, the proximal control mechanism 240 shown provides eight input connections 300. Of course, some input connections may be unused by some surgical instruments.

Figure 4:
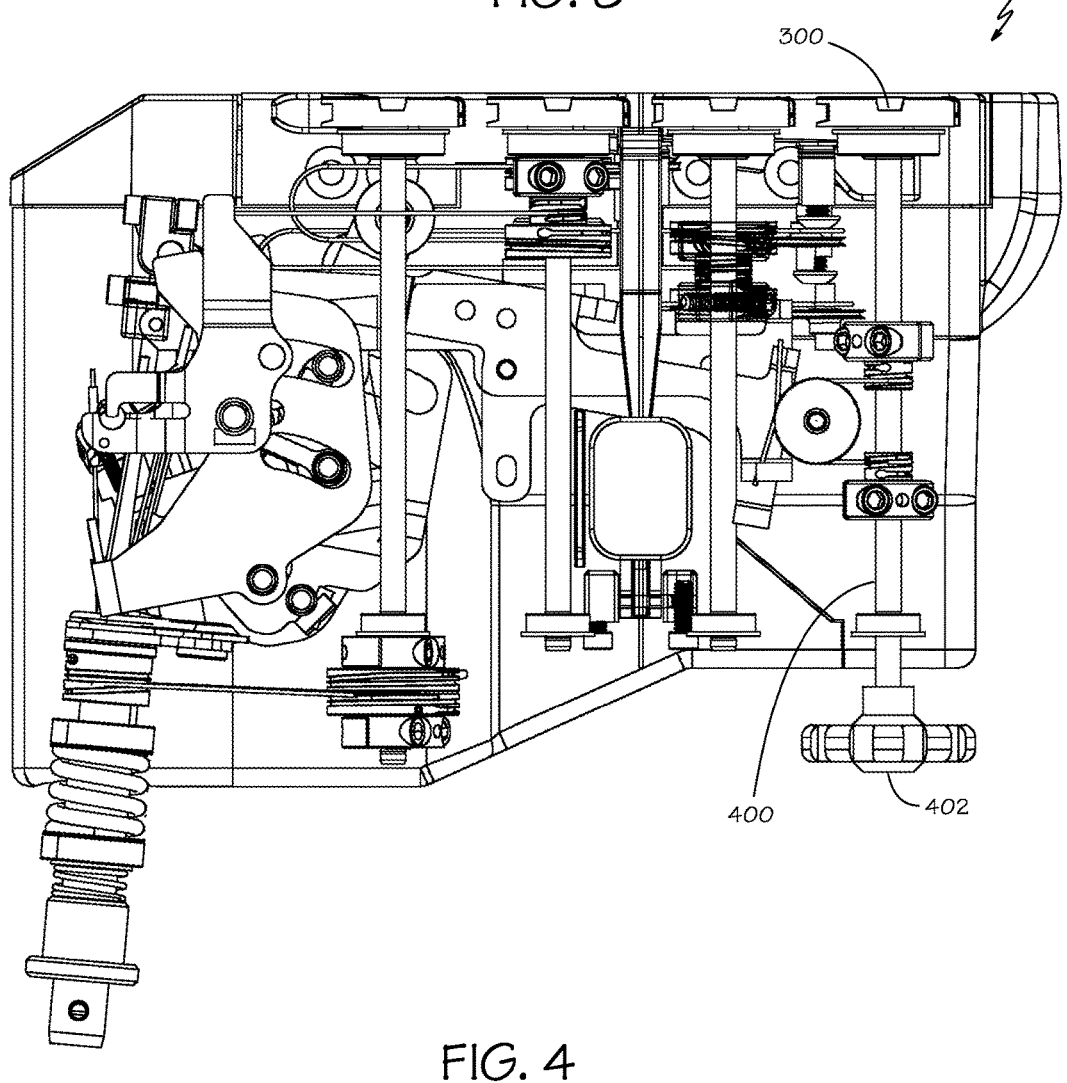
FIG. 4 is a side view of the surgical instrument of FIG. 2 with portions of the housing and support structure removed to show a mechanism for driving a mechanically actuated surgical instrument.

FIG. 4 is a side view of the proximal control mechanism 240 for the surgical instrument of FIG. 2 with portions of the housing and support structure removed to show a mechanism for driving a mechanically actuated surgical instrument. One of the input connections 300 is fixed to an input axle 400 having an input axis about which the input connection rotates. The input axle 400 receives a rotational input from an actuator that is removably coupled to the input connection 300. A hand wheel 402 may be coupled to an opposite end of the input axle 400 from the coupler.

Figure 5A:
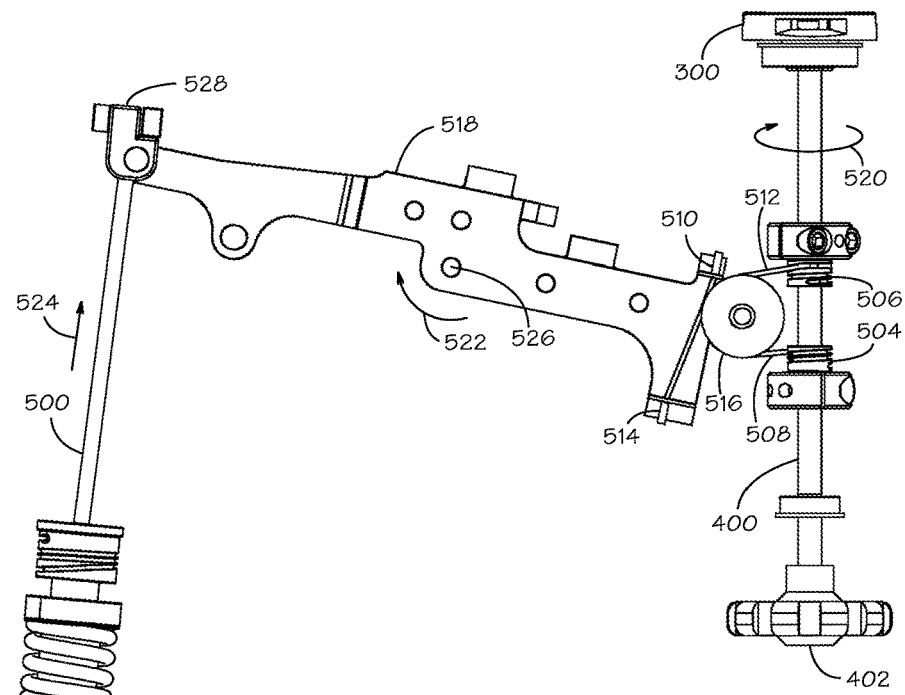
FIG. 5A is a side view of the portion of the surgical instrument of FIG. 4.
Figure 5B:
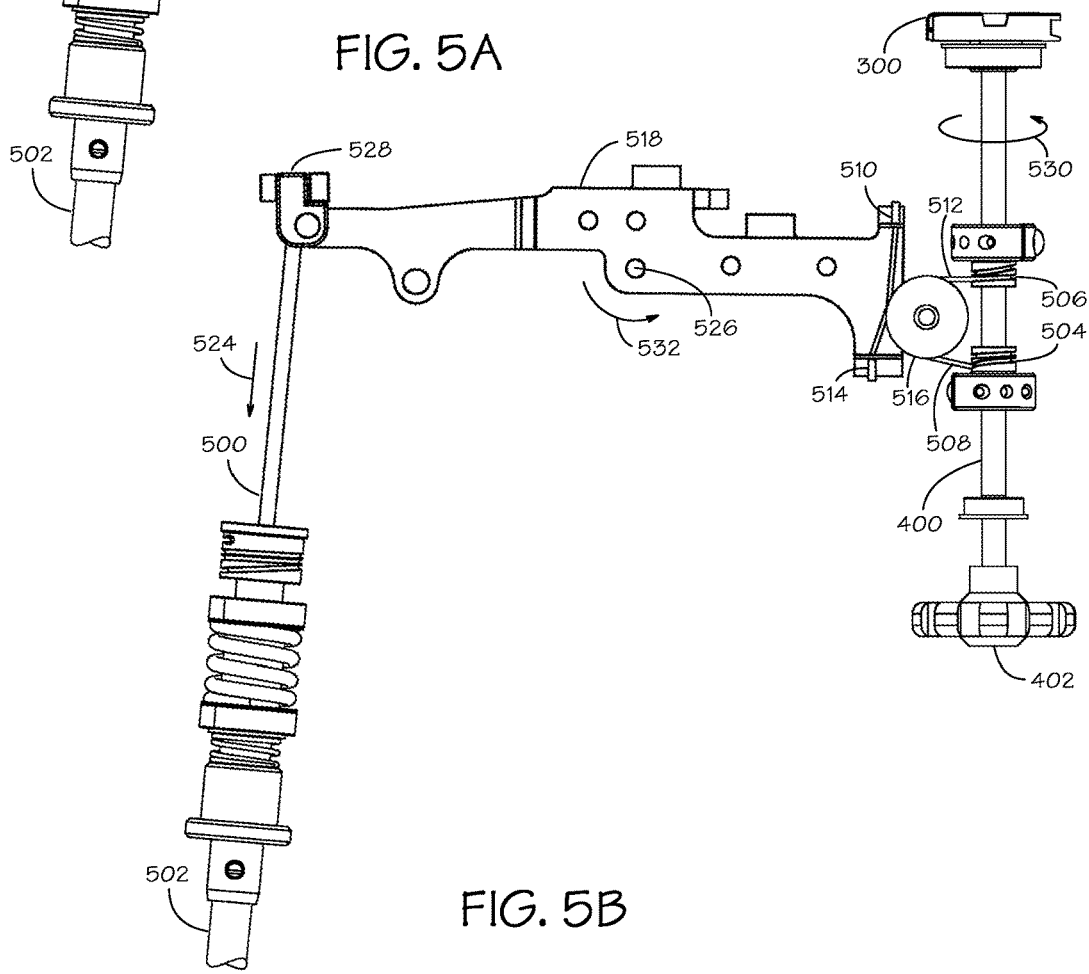
FIG. 5B is the portion of the surgical instrument of FIG. 4 in a second position.

FIGS. 5A and 5B are side views of a portion of the surgical instrument of FIG. 2 shown in two operative positions. The portion shown provides a push-pull drive for a rod 500 that passes through the elongate tube 502 to open and close the surgical instrument. Note that only the proximal end of the elongate tube 502 is shown. The portion of the elongate tube that projects toward the surgical site is not shown.

The input axle 400 has a first axis of rotation along the length of the axle. An input connection 300 for a rotary actuator may be coupled to an end of the input axle 400. A hand wheel 402 may be coupled to an opposite end of the input axle 400 from the input connection 300. A first capstan 504 and a second capstan 506 are fixed to the input axle 400. A first cable 508 passes over an idler pulley 516 with a first end coupled to the first capstan 504 and a second end 510 coupled to a lever 518. The idler pulley 516 has a second axis of rotation substantially perpendicular to the first axis of rotation of the input axle 400. The lever 518 has a third axis of rotation 526 substantially parallel to the second axis of rotation. In another embodiment shown in FIG. 6, the first capstan 604 and the second capstan 606 are portions of a single capstan 600.

As shown in FIG. 5A, rotating the input axle 400 in a first direction 520 winds the first cable 508 onto the first capstan 504 and rotates the lever 518 in a second direction 522. As shown in FIG. 5B, rotating the input axle 400 in a third direction 530 opposite the first direction 520 winds the second cable 512 onto the second capstan 506 and rotates the lever 518 in a fourth direction 532 opposite the second direction. The first cable 508 and the second cable 512 may be portions of a single cable. The lever 518 is coupled to the rod 500 by a linkage 528 to impart a push-pull movement 524 to the rod and thereby transmit a force that can open and close an end effector at the distal end of the elongate tube 502 of a mechanically actuated surgical instrument. In an optional embodiment, a spring (not shown) may be placed between the lever and the support structure to counteract friction in the force transmission mechanism and/or to bias the movable end effector component to one position or another (e.g., grip biased open or closed).

The force transmission may use levers in various arrangements. Different classes of levers provide various advantages in terms of layout, force multiplication, and kinematic relationships. For example, the lever 518 shown in FIGS. 5A and 5B is a first class lever. The fulcrum (axis of rotation 526) is between the applied force 510, 514 and the linkage 528 that couples the load 500 to the lever 518.

Figure 6:
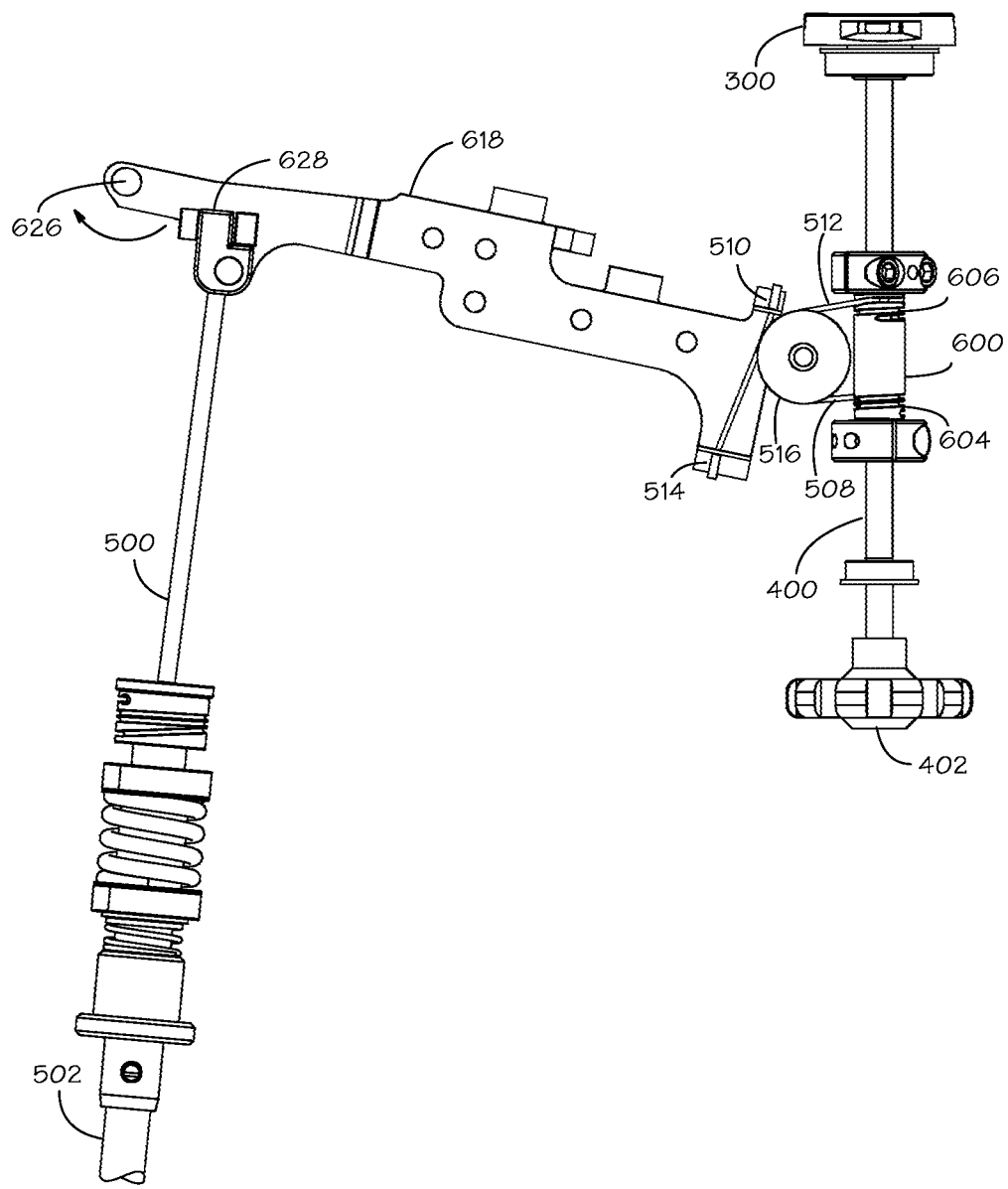
FIG. 6 is a side view of a portion of another surgical instrument that embodies the invention.

FIG. 6 shows a force transmission that uses a second class lever. The linkage 628 that couples the load 500 to the lever 618 is between the applied force 510, 514 and the fulcrum (axis of rotation 626).

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A force transmission comprising:
    an input axle having a first axis of rotation;
    an idler pulley having a second axis of rotation substantially perpendicular to the first axis of rotation;
    a lever having a third axis of rotation substantially parallel to the second axis of rotation;
    a first capstan fixed to the input axle;
    a second capstan fixed to the input axle;
    a first cable that passes over the idler pulley with a first end coupled to the first capstan and a second end coupled to the lever such that rotating the input axle in a first direction winds the first cable onto the first capstan and rotates the lever in a second direction; and
    a second cable that passes over the idler pulley with a third end coupled to the second capstan and a fourth end coupled to the lever such that rotating the input axle in a third direction opposite the first direction winds the second cable onto the second capstan and rotates the lever in a fourth direction opposite the second direction.

2. The force transmission of claim 1 wherein the lever is a first class lever.

3. The force transmission of claim 1 wherein the lever is a second class lever.

4. The force transmission of claim 1 further comprising an input connection for a rotary actuator coupled to an end of the input axle.

5. The force transmission of claim 4 further comprising a hand wheel coupled to an opposite end of the input axle from the input connection.

6. The force transmission of claim 1 further comprising a linkage that couples the lever to a rod that opens and closes an end effector of a mechanically actuated surgical instrument.

7. The force transmission of claim 1 wherein the first cable and the second cable are portions of a single cable.

8. The force transmission of claim 7 wherein the first capstan and the second capstan are portions of a single capstan.

9. A mechanically actuated surgical instrument comprising:
    a surgical end effector;
    an elongated tube coupled to the surgical end effector;
    a rod coupled to the surgical end effector and passing through the elongated tube; and
    a proximal control mechanism coupled to the elongated tube, the proximal control mechanism including
        an input axle having a first axis of rotation,
        an idler pulley having a second axis of rotation substantially perpendicular to the first axis of rotation,
        a lever coupled to the rod and having a third axis of rotation substantially parallel to the second axis of rotation,
        a first capstan fixed to the input axle,
        a second capstan fixed to the input axle,
        a first cable that passes over the idler pulley with a first end coupled to the first capstan and a second end coupled to the lever such that rotating the input axle in a first direction winds the first cable onto the first capstan, rotates the lever, and moves the rod in a second direction, and a second cable that passes over the idler pulley with a third end coupled to the second capstan and a fourth end coupled to the lever such that rotating the input axle in a third direction opposite the first direction winds the second cable onto the second capstan, rotates the lever, and moves the rod in a fourth direction opposite the second direction.

10. The mechanically actuated surgical instrument of claim 9 wherein the lever is a first class lever.

11. The mechanically actuated surgical instrument of claim 9 wherein the lever is a second class lever.

12. The mechanically actuated surgical instrument of claim 9 the proximal control mechanism further including an input connection for a rotary actuator coupled to an end of the input axle.

13. The mechanically actuated surgical instrument of claim 12 the proximal control mechanism further including a hand wheel coupled to an opposite end of the input axle from the input connection.

14. The mechanically actuated surgical instrument of claim 9 wherein the rod opens and closes the surgical end effector.

15. The mechanically actuated surgical instrument of claim 9 wherein the first cable and the second cable are portions of a single cable.

16. The mechanically actuated surgical instrument of claim 15 wherein the first capstan and the second capstan are portions of a single capstan.

17. A method of transmitting force to a mechanically actuated surgical instrument, the method comprising:

rotating an input axle in a first direction to wind a first cable onto a first capstan fixed to the input axle, the input axle having a first axis of rotation;

passing the first cable over an idler pulley having a second axis of rotation substantially perpendicular to the first axis of rotation;

coupling the first cable to a lever to rotate the lever in a second direction, the lever having a third axis of rotation substantially parallel to the second axis of rotation;

rotating the input axle in a third direction opposite the first direction to wind a second cable onto a second capstan fixed to the input axle;

passing the second cable over the idler pulley; and coupling the second cable to the lever to rotate the lever in a fourth direction opposite the second direction.

18. The method of claim 17 wherein the lever is a first class lever.

19. The method of claim 17 wherein the lever is a second class lever.

20. The method of claim 17 further comprising coupling the lever to a rod to close a surgical end effector when the lever is rotated in the second direction and open the surgical end effector when the lever is rotated in the fourth direction.

21. The method of claim 17 wherein the first cable and the second cable are portions of a single cable.

22. The method of claim 21 wherein the first capstan and the second capstan are portions of a single capstan.

* * * * *